United States Patent [19]

Liu

[11] Patent Number: 4,463,204

[45] Date of Patent: Jul. 31, 1984

[54] PROCESS FOR ALKYLATING TOLUENE WITH METHANOL TO FORM STYRENE USING A LOW SODIUM CONTENT POTASSIUM/CESIUM MODIFIED ZEOLITE CATALYST COMPOSITION

[75] Inventor: Huei-Cheng Liu, Oakland, N.J.

[73] Assignee: Exxon Research & Engineering Co., Florham Park, N.J.

[21] Appl. No.: 487,590

[22] Filed: Apr. 22, 1983

[51] Int. Cl.$^3$ ................................................ C07C 1/20
[52] U.S. Cl. ...................................... 585/437; 585/438
[58] Field of Search ................ 585/437, 428, 438, 469

[56] References Cited

U.S. PATENT DOCUMENTS 2,882,244  4/1959  Milten ............................. 252/455 Z
4,140,726  2/1979  Unland et al. ....................... 585/438

FOREIGN PATENT DOCUMENTS 57-68144  4/1982  Japan .

OTHER PUBLICATIONS

Article "The Ion-Exchange Properties of Zeolites, I. Univalent Ion Exchange in Synthetic Faujasite," Howard S. Sherry–J. of Physical Chemistry, vol. 70, pp. 1158–1168 (1966).

Itoh et al., report "Experimental Evidence for the Role of Acidic Sites in the Side-Chain Alkylation of Alkylbenzenes with Methanol, pp. 170–171 of Journal of Catalysis, vol. 72.

Article "Condensation of Toluene and Methanol on Synthetic Zeolites Exchanged with Alkali Ions," Dokl Akad Nauk SSSR, vol. 173, No. 1:132–134.

Article "Alkylation on Synthetic Zeolites," T. Yashima et al.–Journal of Catalysis, vol. 26, 303–312 (1972).

Sodesawa et al., "A Study of Catalysis by Metal Phosphates V. the Alkylation of Toluene with Methanol over Metal Phosphate Catalysis," Bulletin of the Chemical Society of Japan, vol. 52(8), pp. 2431–2432 (1979).

Primary Examiner—Delbert E. Gantz
Assistant Examiner—Cynthia A. Prezlock
Attorney, Agent, or Firm—R. A. Maggio

[57] ABSTRACT

A process for alkylating toluene (or derivative thereof) with methanol to form e.g. styrene and ethylbenzene (or derivatives thereof) using a modified low sodium content zeolite catalyst composition is disclosed. The zeolite catalyst composition is exemplified by a type X- or Y-zeolite modified with potassium and cesium through a sequential exchange.

13 Claims, No Drawings

PROCESS FOR ALKYLATING TOLUENE WITH METHANOL TO FORM STYRENE USING A LOW SODIUM CONTENT POTASSIUM/CESIUM MODIFIED ZEOLITE CATALYST COMPOSITION

BACKGROUND OF THE INVENTION

The present invention is directed to catalyst compositions and processes for reacting toluene and methanol to form styrene.

Styrene is currently commercially produced from benzene in a two-step process. In the first step benzene is alkylated with ethylene to form ethylbenzene, and in the second stop, the ethylbenzene is dehydrogenated to form styrene.

For example, the alkylation of aromatic compounds with olefins, alkyl halides and alcohols in the presence of a rare earth metal (including cerium) modified X- or Y-type zeolite is broadly disclosed in U.S. Pat. No. 3,251,897. Such alkylations are non-specific to styrene, the predominant reaction disclosed being benzene+ethylene to form ethylbenzene. Thus, such zeolite catalyzed reactions can be employed to make ethylbenzene in the first stage of conventional styrene synthesis.

One of the known alternative routes for forming styrene involves the oxidative coupling of toluene to form 1, 2-diphenyl ethylene (stilbene) followed by the disproportionation of the stilbene with ethylene in the presence of a catalyst to form styrene. The economic significance of the overall process scheme of the toluene-stilbene-styrene route resides in the fact that styrene can be produced from 0.5 mole of ethylene and one mole of toluene. This compares with the conventional ethylbenzene route wherein styrene is produced from one mole of ethylene and one mole of benzene.

In light of the rising costs of benzene and ethylene and the environmental problems of benzene, toluene-based processes will become a more attractive route than the existing benzene-based process for styrene manufacture.

Representative catalysts employed in the toluene to stilbene route for styrene synthesis are metal oxides such as those disclosed in U.S. Pat. Nos. 3,694,518; 3,739,038; 3,868,427; 3,965,206; 3,980,580; 4,091,044; 4,183,828; 4,243,825; 4,247,727; 4,254,293; 4,255,602; 4,255,603; 4,255,604; 4,268,703; 4,268,704; 4,278,824; 4,278,825; and 4,278,826 all assigned to Monsanto.

Commonly assigned U.S. patent application Ser. No. 405,803 now U.S. Pat. No. 4,429,174, filed Aug. 6, 1982 by H. Teng and I. Huang employs a faujasite zeolite modified with Li, K, Rb or cesium cations and at least one promoter selected from the group consisting of B, P, Pb, Cu, Zn, Ni, O, and Fe for the toluene to stilbene route.

A separate and distinct alternative route to styrene from toluene involves the alkylation of the side chain of toluene with methanol or formaldehyde by contact of these reactants with X- or Y-type zeolites, as described in Yashima et al in the Journal of Catalysis, Vol. 26, 303–312 (1972). More specifically, it is disclosed therein that alkylation of the methyl group of toluene to form styrene and ethylbenzene is effected by Na, K, Rb or Cs exchanged X- or Y-type zeolites, whereas Li exchanged zeolites of the same type effected predominantly the alkylation of the benzene ring of toluene to form xylenes. Yashima et al interpret their results as suggesting that xylene production is attributable to the acidity of the catalyst, whereas styrene and ethylbenzene formation is attributable to the basicity of the catalyst. At page 309 of Yashima et al, the authors discuss the effect on catalyst activity as a function of the percentage of ion exchange of a potassium exchanged X-type zeolite. The data presented at Table 3 therein indicates that styrene yield increases up to about a 60% potassium exchange but levels off at higher percentages of such potassium exchange. Yashima et al conclude that while the yield of $C_8$ aromatics increases substantially with the percentage of K ion exchange up to about 60%, no marked increase is observed above this level of exchange. Yashima et al also conclude that a cesium exchanged X-type zeolite has a lower activity for toluene alkylation than, for example, a potassium exchanged X-type zeolite because of partial destruction of the zeolite crystallinity in the cesium exchanged zeolite. Yashima et al do not test or prepare a CS/K exchanged zeolite.

Sidorenko et al in the article "Condensation of Toluene and Methanol on Synthetic Zeolites Exchanged with Alkali Ions", Dokl. Akad. Nauk SSSR, Vol. 173 No. 1:132–34 (1967), have proposed a mechanism for the alkylation of toluene with methanol using alkali metal exchanged X- and Y-type zeolites wherein methanol is converted to formaldehyde which then reacts with toluene to produce styrene and ethylbenzene. Sidorenko et al test the following alkali metal exchanged type-X or type-Y zeolites: Li/Na-X, K/Na-X, Li/Na-Y, K/Na-Y, Rb/Na-Y, Cs/Na-Y, Rb/Na-X; but do not test K/Cs/Na-X or -Y type zeolites.

Since alkali metal exchanged zeolites are capable of catalyzing a variety of reactions and therefore produce a variety of by-products, the selectivity of the toluene to styrene is very low when conducting the process in accordance with Yashima et al or Sidorenko et al.

In an effort to improve the selectivity of the toluene/methanol alkylation reaction to styrene, Unland et al, U.S. Pat. No. 4,140,726 (a division of U.S. Pat. No. 4,115,424) describe the use of an X- or Y-type zeolite which has been modified by a cation exchange with one or more of potassium, rubidium and cesium and impregnated with boron or phosphorus. At Col. 3, lines 49 et seq. it is disclosed that (1) in theory only 81% of the sodium in type-X zeolite and 71% of the sodium in type-Y zeolite is exchangable with one or more of potassium, rubidium or cesium; (2) usual exchange procedures do not readily produce Na exchanges above about 60%; and (3) no improvement is observed above about a 60% Na exchange. Furthermore, Unland et al never actually prepare or test a K/Cs/Na-X or -Y type dual ion exchanged zeolite with or without B and/or phosphorus.

Itoh et al report in J. of Catalysis, Vol. 72, p. 170 (1981) the use of Rb, K, Li cation exchanged X-type zeolites, such as Rb/Li-X, Rb-X and Rb/K-X, for the side chain alkylation of p-xylene with methanol to produce p-methylstyrene and p-ethyltoluene. A maximum 68 mole % conversion of methanol with mole % yields of 5.3% (p-methylstyrene) and 2.7% (p-ethyltoluene) are disclosed. Itoh et al, however, do not prepare or test a K/Cs/Na-X or Y-type dual ion exchanged zeolite.

Japanese Patent Application Publication No. Sho 57-68144 published April 26, 1982 is directed to catalyst for styrene synthesis which comprises a zeolite of the faujasite class having at least 20% of the sodium cations present therein exchanged with cesium, potassium or rubidium and which has been treated to impregnate therein one or more divalent or trivalent metal salts of boric or phosphoric acid, the metal of said salt disclosed as being selected from magnesium, calcium, aluminum, magnanese, iron, cobalt, nickel, copper and zinc. In Comparative Example 4 thereof, a Cs exchanged X-type zeolite is impregnated with $K_3PO_4$. This catalyst is used for comparative purposes and produces a methanol conversion of 71%, a styrene and ethylbenzene selectivity of 42.1% and a styrene to styrene+ethylbenzene ratio of 0.56. This Japanese patent publication refers to Unland et al, U.S. Pat. No. 4,115,424 for its description of the method of effecting ion exchange. Thus, the limitations on the percentage and effect of exceeding a 60–65% Na exchange of Unland et al are, in effect, incorporated into the Japanese patent publication. Futhermore, it is noted that the amount of potassium in the phosphate salt employed in the impregnation of the zeolite of Comparative Example 4 of the Japanese patent publication is determined by the amount of phosphorus sought to be impregnated into the zeolite not on the amount of sodium sought to be replaced in the zeolite by potassium.

U.S. Pat. No. 2,882,244 discloses the composition and preparation of zeolite X. At Col. 6, lines 15 et seq. it is disclosed that the adsorbents contemplated in this patent include not only the sodium form of the zeolite but also crystalline materials obtained from such zeolite by partial or complete replacement of sodium with other cations. At Col. 7, lines 28 et seq. it is stated that "by varying the concentration of the zinc or other exchange ion in solution, or by varying the time allowed for ion exchange, or by varying the temperature, the exchange ion may replace up to nearly 100% of the sodium ions".

Contrary to the above assertions, it is known that not all cations can effect a complete sodium exchange, cesium cations being one example (See, Unland et al). Thus, except by specific example, this patent does not teach which of the numerous potential cations disclosed therein can, in fact, effect complete or substantially complete ion exchange of sodium. Futhermore, in the examples, neither potassium nor cesium is employed in an actual exchange procedure resulting in complete or substantially complete sodium replacement. This patent does not suggest the use of any of the zeolites disclosed therein for the side chain alkylation of toluene and the like reactions.

U.S. Pat. No. 3,251,897 discloses the use of X- or Y-type zeolites for direct alkylation of aromatic compounds, e.g. benzene is reacted with ethylene to form ethylbenzene. As discussed above, this reaction is completely different from the side chain alkylation of alkylated aromatic compounds. The zeolites employed in the process of this patent are subjected to an exchange with rare earth cations. Such rare earth exchanges result in a sodium content of between about 5 and about 0.2 wt. based on the zeolite weight. The use of alkali metal exchanges is not disclosed.

Howard S. Sherry reported in his article "The Ion-Exchange Properties of Zeolite. I. Univalent Ion Exchange in Synthetic Faujasite", J. of Physical Chemistry, Vol. 70, pp. 1158–1168 (1966) the results of a study of the ion exchange of Linde X and Y zeolites. From ion-exchange isotherm data describing the exchange of Li, K, Rb, Cs, Ag, or Tl ions into Linde Na-X; he concluded that below a 40% replacement of Na ion the selectivity series is $Ag>>Tl>Cs\geqq Rb>K>Na>Li$, e.g. potassium is preferred over sodium. However, above a 40% replacement of the Na ion the selectivity series becomes $Ag>>Tl>Na>K>Rb\geqq Cs>Li$, e.g. sodium is preferred over potassium. Thus, it would appear difficult at high degrees of ion-exchange, to replace sodium with potassium ions. All of the exchanges conducted in Sherry are mono exchanges, i.e., only a single ion is exchanged for sodium in each exchange experiment. When conducting the exchanges on Linde Na-Y zeolites, a preference for Na over K is also described. Sherry also discusses the limitations of a cesium exchange to replace sodium.

Japanese Kokai 52-133, 932 published Nov. 9, 1977, discloses the use of a catalyst, formed by impregnating activated carbon with oxides of potassium, rubidium, cesium, or francium and mixtures thereof, for alkylating side chains of alkyl aromatic compounds with methanol.

Sodesawa et al, "A Study of Catalysis by Metal Phosphates V. the Alkylation of Toluene with Methanol over Metal Phosphate Catalysts", Bulletin of the Chemical Society of Japan, Vol. 52(8) pp. 2431–2432 (1979) disclose the use of catalysts, for the subject conversion reaction, of $Ca_3(PO_4)_2$ or $K_3PO_4$ supported on active carbon gave more ethylbenzene than the use of MgO.

Russian Patent No. 272299 discloses a process for alkylating toluene with formaldehyde using a sodium based type-X zeolite which has been partially exchanged with potassium, rubidium, or cesium.

From the above prior art discussion, it is observed that basic sites on the X- or Y-type zeolites are believed to be important for the side chain alkylation of toluene with methanol. Yashima et al recognized that the basicity of such zeolites depends of the basicity of the alkali metal cation in the zeolite, i.e. arranging the alkali metals in their increasing order of basicity they conclude $Na<Rb<Cs$. However, Yashima et al teach away from using cesium to control basicity of the zeolite, because of alleged destruction of the zeolite crystallinity by a cesium exchange. Even when one attempts to use cesium to control zeolite basicity, there are limits to the degree to which one can replace sodium with cesium cations as reported by Unland et al. This was not considered a problem by Unland et al since they failed to appreciate that any practical benefit could be obtained at exchange rates above about 60% of the sodium. Consequently, conventional wisdom in this area has been not even to attempt to exceed a sodium exchange rate above 60%.

Notwithstanding the above, the search has continued for catalyst compositions capable of improving the conversion and/or styrene selectivity of toluene side chain alkylation reactions with methanol. The present invention was developed in response to this search.

SUMMARY OF THE INVENTION

In accordance with the present invention, it has been found that it is possible to replace between about 80 and about 90 %, by weight, of the sodium content present in crystalline aluminosilicates, e.g., X- and Y-type zeolites, with a combination of potassium and cesium cations, and that by effecting such a high sodium exchange, the toluene conversion, and ethylbenzene+styrene selectivity can be substantially improved. It is believed that the difficulty in obtaining a high cesium exchange for sodium is due to the interaction of sodium and oxygen in the supercage of the zeolite, and the fact that the sodalite cage containing the sodium interior to the zeolite is too small to admit cesium for exchange with the sodium. Consequently, one observes a maximum practical cesium exchange of about 60 to 65% of the initial sodium content. While the process of the present invention does not result in a cesium exchange above this level, it has been found that improved catalyst performance can be achieved by the balance of basicity imparted to the zeolite when between about 80 and about 90% of the sodium in a sodium based X or Y-type zeolite is replaced by a combination of cesium and potassium. Potassium cations are more readily accessible to the sodalite cage even at the interior of the zeolite than cesium. Consequently, by conducting a sequential cation exchange of potassium first, followed by cesium, it has been found possible to replace most of the zeolite sodium with potassium. The potassium is then partially exchanged with cesium in a second exchange procedure. In this way the maximum basicity associated with the highly basic cesium cation can be imparted to the zeolite, while further enhancing the basicity of cationic sites inaccessible to the cesium cations with potasssium.

Accordingly, in one aspect of the present invention there is provided a process for alkylating toluene or toluene derivative with at least one alkylating agent which comprises reacting said alkylating agent with at least one compound represented by the structural formula:

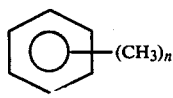
(I)

wherein n is a number which can vary from 1 to 6, said reaction being conducted in the presence of a catalyst composition comprising a crystalline aluminosilicate zeolite of the faujasite structure, under conditions sufficient to form a product comprising at least one compound represented by the structural formulae:

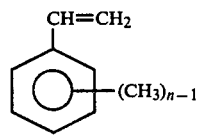
(II)

and

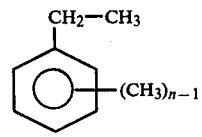
(III)

wherein n is a number which corresponds in value to that employed for n in structural formula I, and wherein in said crystalline aluminosilicate zeolite the $SiO_2:Al_2O_3$ mole ratio is from about 2 to about 8, and the electrovalence of the tetrahedra containing aluminum present therein is balanced by the inclusion in the crystal zeolite structure of cations comprising potassium and cesium which cations are present in amounts sufficient to achieve a potassium to aluminum mole ratio of from about 0.40:1 to about 0.60:1, and a cesium to aluminum mole ratio of from about 0.45:1 to about 0.30:1.

Methylations of toluene with methanol can produce some methanol decomposition products, and over certain conventional catalysts are capable of producing various xylenes or other alkylated aromatics, as well as some polymer, aromatization and coke materials, along with the styrene and ethylbenzene sought in the process of the present invention. The present invention provides a means of directing the process toward the production of styrene and ethylbenzene (or derivatives thereof when employing toluene derivatives in the feed). The use of the catalysts of the present invention increases the selectivity and/or yield to styrene+ethylbenzene, relative to the use of a catalyst lacking potassium or cesium or catalysts in which the potassium or cesium is present in less than the required amounts specified herein.

DESCRIPTION OF PREFERRED EMBODIMENTS

In accordance with the process of the present invention toluene or a toluene derivative is contacted with methanol in the presence of a catalyst composition, comprising zeolite catalysts modified with cesium and potassium, to form styrene.

More specifically, zeolites, which are crystalline in nature, are known for the alkylation of toluene to styrene and ethylbenzene. It has been found that such zeolites can be modified as taught herein to provide improved catalysts for such reactions. For example, the X- or Y-type zeolites described in U.S. Pat. Nos. 3,251,897 and 4,140,726, as well as those described in the Journal of Catalysis, Yashima et al, Vol. 26, 303–312 (1972) may be employed as described herein.

In general, suitable zeolites which can be modified in accordance with the present invention preferably will be of the faujasite structure with a $SiO_2:Al_2O_3$ mole ratio in the range of about 2 to about 8. With regard to structural classification, those zeolites with a double 6-ring, or faujasite structure, are generally suitable for use herein. Such zeolites characteristically have pore diameters of at least 6 angstroms, preferably at least 8 angstroms (e.g. 6 to 15 angstroms), which is appropriate for admission of toluene and derivatives thereof, and to allow exit of styrene and ethylbenzene. The X- and Y-type zeolites have been found very suitable for modification and use herein, with the X-type being particularly preferred.

The description and method of preparation of X- and Y-type zeolites is provided in U.S. Pat. No. 2,882,244 (X-type zeolite) and U.S. Pat. No. 3,130,007 (Y-type zeolite).

Zeolites X and Y consist basically of a three-dimensional framework of $SiO_4$ and $AlO_4$ tetrahedra. The tetrahedra are cross-linked by the sharing of oxygen atoms so that the ratio of oxygen atoms to the total of the aluminum and silicon atoms is equal to two or $O/(Al+Si)=2$. The electrovalence of each tetrahedra containing aluminum is balanced by the inclusion in the crystal of a cation, such as sodium. Although there are a number of other cations that may be incorporated into X and Y zeolites during synthesis thereof, such zeolites typically are commercially available in the sodium form due to the ease of synthesis thereof.

Type-X zeolite can be represented in terms of mole ratios of oxides as follows:

$$1.0\pm0.2Z_{2/n}O:Al_2O_3:2.5\pm0.5SiO_2:YH_2O \qquad (I)$$

wherein Z is at least one cation and each cation representing Z has a valence of not more than 3, n represents the valence of each Z, and Y is a value up to 8, depending on the identity of Z and the degree of hydration of the crystal. A sodium form of zeolite X preferred for use herein may be represented in terms of mole ratios of oxides as follows:

$$Na_2O:Al_2O_3:2.5SiO_2:6H_2O \qquad (II)$$

although the mole ratio of $SiO_2:Al_2O_3$ can typically vary from about 2:1 to about 3:1.

Zeolite Y differs from zeolite X in that it contains more silica and less alumina. Consequently, due to its higher silica content this zeolite has more stability to the hydrogen ion than zeolite X.

The sodium form of zeolite Y, may be represented in terms of mole ratios of oxides as follows:

$$0.9\pm0.2Na_2O:Al_2O_3:WSiO_2:XH_2O \qquad (III)$$

wherein "W" is a number having a value of typically from about 3 to about 8, preferably 3 to about 6, and "X" is a number having a value up to about 9.

The selectivity of zeolite Y for larger molecules is appreciably the same as zeolite X because its pore size extends from 10 to 13 angstrom units.

Type L zeolites and natural faujasite materials are examples of other zeolites having appropriate pore size and structure for use herein. In general, zeolites having suitable properties can be utilized, whether obtainable as natural materials or prepared synthetically, and can be obtained from commercial sources or prepared by appropriate laboratory crystallization procedures.

The zeolites described hereinabove are modified by sequentially exchanging the cationic sites of the zeolite with potassium and then cesium. The sequential ion exchange is conveniently conducted by conventional ion exchange procedures using a fluid medium to partially replace therewith, the sodium, hydrogen or other inorganic cations normally present in the zeolite. Any medium which will ionize the cation without adversely affecting the zeolite may be employed for exchange. Heating of the exchange solution to temperatures of from about 80 to about 100° C. is preferred to facilitate the ratio of ion exchange. Typically, aqueous and/or organic, preferably aqueous, solutions of the alkali metals, i.e. K and Cs, are employed for this purpose. Metal compounds which can be solubilized in aqueous or organic media for ion exchange include alkali metal: halides, hydroxides, nitrates, acetates, and mixtures thereof.

In addition to water, any organic medium, preferably a volatile organic medium, which permits ion exchange, of said alkali metal, can be employed, including such organic solvents as alcohols, ketones, ethers, amides and other polar organic solvents, and mixtures thereof.

Representative of such organic solvents include acetone, methanol, ethylene glycol, isopropanol, isobutanol, diethylether, benzene, toluene, dimethyl formamide, tetrahydrofuran, methylethyl ketone, methylbutyl ketone, and mixtures thereof.

To facilitate alkali metal exchange, some of the Na ions in the zeolite can be partially replaced initially with hydrogen ions. The hydrogen ions are more readily displaced by the alkali metal ions than sodium ions. This replacement may be accomplished by treatment of the zeolite with a fluid medium containing a hydrogen ion or an ion capable of conversion to a hydrogen ion. Inorganic and organic acids represent the source of hydrogen ions, whereas ammonium compounds are representative of the cations capable of conversion to hydrogen ions. Care should be taken to assure that all of the hydrogen ions so introduced in place of sodium are eventually replaced with the alkali metals since the protons can undesirably reduce the basicity of the catalyst.

The sequential potassium and cesium exchange is conducted to replace typically at least 80%, preferably at least 85% and most preferably at least 90%, of the exchangable cations initially present in the zeolite with potassium and cesium. The exchangable cations of the zeolite include not only sodium but also any cation which can occupy a cationic site in place of sodium, such as hydrogen.

In the first stage of the exchange, potassium typically will replace from about 80 to about 90%, and preferably from about 85 to about 90% of the sodium cations in the zeolite. In the second stage of the exchange, the sodium content typically will remain the same as resulting from the first stage and the cesium will replace typically from about 30 to about 50%, and preferably from about 30 to about 40% of the potassium resulting from the first exchange.

If the sequence of exchange is reversed, i.e. cesium followed by potassium, the potassium will replace some of cesium in addition to the sodium. This is undesirable since it is sought to maximize the cesium content of the zeolite to which is attributable the greatest increase in catalyst perfomance. Thus, by maximizing the cesium content and minimizing the sodium content with potassium, a still further increase in catalyst performance is obtained.

Simultaneous exchange of sodium for cesium and potassium is also disadvantageous in that a maximum cesium content is not achieved.

The acid-base properties of the zeolite responsible for enhanced selectivity and/or yield are affected not by the alkali metal content of the zeolite in isolation, but by the balance established between said alkali metal content and the aluminum content in the zeolite by the exchange. Consequently, the most convenient way to express the alkali metal content sought to be imparted to the zeolite is as an alkali metal:alumina mole ratio.

Accordingly, the ion-exchange is conducted to impart to the zeolite (1) a potassium to aluminum mole ratio of typically from about 0.40:1 to about 0.60:1, preferably from about 0.50:1 to about 0.60:1, and most preferably from about 0.55:1 to about 0.60:1; and (2) correspondingly a cesium to aluminum mole ratio of typically from about 0.45:1 to about 0.30:1, preferably from about 0.40:1 to about 0.30:1, and most preferably from about 0.35:1 to about 0.30:1. The residual cationic sites typically are occupied by sodium cations.

When an X- or Y-type zeolite is subjected to an exchange in accordance with the process described herein, the residual sodium:aluminum mole ratio imparted to the zeolite typically will vary from about 0.1:1 to about 0.2:1, preferably from about 0.1:1 to bout 0.15:1, and most preferably from about 0.1:1 to about 0.12:1.

An alternative way to express the alkali metal content imparted to the zeolite is on a weight percentage basis. Accordingly the potassium exchange is conducted to impart a potassium content to the zeolite of typically from about 10 to about 16, preferably from about 14 to about 16, and most preferably from about 15 to about 16%, by weight potassium on an elemental basis, based on the total final zeolite catalyst composition weight.

The cesium exchange is conducted to impart a cesium content to the zeolite of typically from about 10 to about 30, preferably from about 20 to about 30, and most preferably from about 25 to about 30%, by weight cesium on an elemental basis, based on the total weight of the final zeolite catalyst composition.

The aforedescribed potassium and cesium exchanges will result in a residual sodium content in the zeolite of typically from about 0.5 to about 4.0, preferably from about 0.5 to about 2.0, and most preferably from about 0.5 to about 1%, by weight Na, on an elemental basis, based on the total weight of the zeolite subsequent to modification, the remainder of the cationic sites in the zeolite preferably being occupied by K and Cs.

To avoid loss of the modifying components by leaching or exchange, it is generally preferred to avoid excessive washing or similar procedures subsequent to modification. Also it is undesirable to subject the catalyst to treatments known to cause loss of cations by exchange with hydrogen or other ions.

The modified zeolite catalyst is generally dried following impregnation procedures typically at temperatures of from about 80° to about 150°, preferably from about 90° to about 120°, and most preferably from about 100° to about 110° C., although drying is optional.

The modified zeolite composition is preferably calcined prior to use. Calcination can be conducted in a separate step or in-situ in the reactor and involves heating the modified zeolite catalyst composition.

Calcination is a heat treatment wherein the solid state structure of the catalyst is fixed. Chemical elements composing the catalyst composition are fixed in a matrix.

Accordingly, calcination is conducted at temperatures of typically from about 300° to about 600°, preferably from about 400° to about 500°, and most preferably from about 400° to about 450° C., for a period of typically from about 1 to about 24, preferably from about 2 to about 16, and most preferably from about 4 to about 16 hours. In conducting calcination, the catalyst is typically heated to the selected calcination temperature(s), at a rate of preferably not greater than about 10° C./min, and most preferably not greater than about 5° C./min.

The atmosphere under which calcination is conducted typically comprises any one or more of air, nitrogen, argon, helium and the like. Although not essential, it is preferred that the calcination atmosphere be passed as a moving stream over the catalyst composition.

The modified zeolites described herein after calcination typically will possess an average pore size of typically from about 6 to about 15, and most preferably from about 8 to about 13 (e.g. 10 to 13) angstroms in diameter.

The modified zeolite catalyst is adaptable to use in the various physical forms in which catalysts are commonly used as particulate material in a contact bed, or a coating material on monolithic structures generally being used in a form to provide high surface area. The catalyst, can if desired, be composited with various catalyst binder or support materials which do not adversely affect the catalyst or the reactions in which the catalyst is to be employed.

The modified zeolite compositions described herein exhibit unexpected activity and styrene selectivity vis-a-vis the side chain alkylation of toluene. Accordingly, conditions generally used in side chain alkylation of toluene with methanol in the presence of conventional zeolite catalysts can be employed. The particular reaction conditions selected will be influenced by such considerations as activity, and temperature stability of the catalyst, desired conversion, and attainable product selectivity.

The toluene alkylation reaction is preferably carried out in the vapor phase and under the influence of heat, although liquid phase reaction can also be employed. The temperature range under which the reaction can be carried out typically will range from about 300 to about 550, preferably from about 380° to about 480° C., and most preferably from about 400° to about 450° C.

Pressure is not critical in the alkylation process of this invention although it is known that very high pressures can suppress methanol decomposition and thereby improve selectivity. Thus, the reaction may be carried out at subatmospheric, atmospheric, or superatmospheric pressures as desired, although the pressure will typically be selected in conjunction with the reaction temperature to assure the reactants are in the vapor phase when contacting the catalyst. It will be generally preferred, however, to conduct the reaction at pressures of typically from about 1 to about 70, preferably from about 25 to about 70, and most preferably from about 50 to about 70 atmospheres.

The process of this invention is conveniently carried out in an apparatus of the type suitable for carrying out chemical reactions in the vapor phase. It can be conducted in a single reactor or in multiple reactors using either a fixed bed, a moving bed, or a fluidized bed system to effect contacting of the reactants and the modified zeolite composition. The reactants, e.g., toluene or toluene derivatives and methanol, will generally be heated and introduced into the reactor as a vapor. However, the reactant may be introduced to the reactor as a liquid and then vaporized.

The reaction time for the contact of the reactants with the modified zeolite composition in the present invention may be selected from a broad operable range which may vary from about 0.4 to about 8, preferably from about 1 to about 5, and most preferably from about 2 to about 4 seconds. The reaction time may be defined as the length of time in seconds which the reactant gases measured under reaction conditions, are in contact with the modified zeolite composition in the reactor. The selected reaction time may vary depending upon the reaction temperature and the desired toluene conversion level. At higher temperatures and lower toluene conversion levels, shorter contact times are required, For example, the reactant feedstream may be passed over the catalyst at a gas hourly space velocity (GHSV) of typically from about 450 to about 9000, preferably from about 720 to about 3600, and most preferably from about 900 to about 1800 $hr^{-1}$.

The reactant feedstream will typically comprise toluene and methanol. The respective amounts of toluene and methanol supplied to the reactor may be specified as a mole ratio of the same. On this basis the mole ratio of toluene: methanol supplied to the reaction zone is typically controlled to be from about 1:0.05 to about 1:20, preferably from about 1:0.1 to about 1:10 (e.g. 1:2 to about 1:10), and most preferably from about 1:0.25 to about 1:5 (e.g. 1:2 to about 1:5). It is an advantage of the present invention that amounts of methanol in excess of stoichiometric amounts (i.e. toluene:methanol mole ratio of 1:1) can be employed without significantly sacrificing styrene+ethylbenzene yield while at the same time substantially increasing toluene conversion relative to low toluene concentrations in the feed stream.

In addition to the aforedescribed reactants, other inert diluent gases such as nitrogen, argon, carbon dioxide, helium and the like are also preferably introduced into the reactor. Such inert gases may be introduced to the process alone or may be combined with the other materials of feed. Preferably the inert gas is introduced to the reaction zone in a manner sufficient to achieve a mole ratio of toluene:inert gas therein of typically from about 0.4:1 to about 5:1, preferably from about 0.5:1 to about 2:1, and most preferably from about 0.75:1 to about 2:1. The preferred inert gas in nitrogen.

While the present invention is described in conjunction with the side chain alkylation of toluene, methyl substituted derivatives of toluene can also be employed for such side chain alkylation thereof. Thus, the hydrocarbon feed source which can be employed in the process of the present invention comprises at least one compound represented by the structural formula:

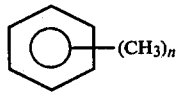  (I)

wherein n is a number from 1 to 6, preferably 1 to 4, most preferably 1 to about 3, (e.g. 2). Representative examples of such hydrocarbon feed sources suitable for alkylation in addition to toluene, include o-xylene, m-xylene, p-xylene, 1,3,5-trimethylbenzene, 1, 2,4-trimethylbenzene, 1,2,4,6-tetramethylbenzene, hexamethylbenzene, pentamethylbenzene and the like. The most preferred toluene derivatives are the xylenes.

Generally, when a hydrocarbon feed source for alkylation other than toluene is employed, the alkylated product will be the appropriate methyl substituted styrene or ethylbenzene products, e.g. the methyl groups in excess of 1 are carried along and remain uneffected by the alkylation reactions.

The term "toluene derivative" is therefore defined herein to be at least one compound represented by formula I wherein n is between 2 and 6.

Furthermore, while the present invention has been described in connection with methanol as the alkylating agent, other alkylating agents may be employed under the same range of conditions. Thus, formaldehyde and/or various forms or sources of formaldehyde can be employed as the alkylating agent including trioxane, methylal, paraformaldehyde, or commercial formaldehyde solutions, such as Formcel formaldehyde solution (55% formaldehyde, 10% water and the balance methanol). The term "alkylating agent" as defined herein is therefore intended to describe any one or more of the abovedescribed materials in addition to methanol.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples and unless otherwise specified, selectivity and conversion are calculated as follows:

$$\text{Selectivity \%} = \frac{\text{moles of desired product}}{\text{moles of toluene reacted}} \times 100$$

$$\text{Toluene Conversion \%} = \frac{\text{moles of toluene reacted}}{\text{moles of toluene in feed}} \times 100$$

$$\text{Yield \%} = \frac{\text{Selectivity (\%)} \times \text{Conversion (\%)}}{100}$$

$$\text{Methanol Conversion \%} = \frac{\text{moles of methanol reacted}}{\text{moles of methanol in feed}} \times 100$$

EXAMPLE 1

A potassium/cesium modified zeolite-X composition of the sodium form was prepared as follows by a multiple sequential ion-exchange technique as follows:

Part A

An aqueous potassium hydroxide solution was prepared by dissolving 56.82 g of KOH in 300 ml of deionized water at room temperature (20° C.). The resulting solution was divided into three 100 ml portions which were successively admixed (in the absence of stirring) with a 20 g sample of Davison 4-8 mesh beads of sodium formed 13X zeolite to form three slurries. Each slurry was allowed to soak at 90° C. for different periods, namely, 5, 16, and 7 hours respectively, and the liquid portion of each slurry was removed from the zeolite before adding the next portion. The resulting potassium exchanged zeolite was washed with 100 ml of water 5 times and then dried in air at 110° C. for 64 hours. A portion of the resulting material was removed for elemental analysis and found to contain Na (1.15%); K (15.66%); Al (11.91%); Si (17.98%) on a weight percentage basis.

Part B

About 12.6 g of the potassium exchanged zeolite from Part A were mixed with 200 ml of an aqueous cesium hydroxide solution prepared by mixing 33 g of $CsOH.XH_2O$ (83%) (0.18 moles CsOH) with 200 ml of water. The mixture was allowed to stand without stirring at 90° C. for 24 hours. The resulting zeolite was filtered and dried at 100° C. in air for 7 hours. A portion of the K/Cs exchanged zeolite was removed for elemental analysis.

The results of the elemental analysis are supplied at Table 1.

Part C

Ten cc of the dried K/Cs modified zeolite sample from Part B were placed into a 40 cc vertical quartz reactor (0.5" O.D., and ⅜" I.D.) stoppered at the bottom with glass wool. About 15 cc of the reactor above the catalyst was filled with glass wool which serves as a preheating zone. Heat was supplied to the reactor with a tubular furnace. The catalyst sample was calcined in-situ by passing $N_2$ gas through the reactor at a rate of 200 cc/min. for 1 hour. The temperature of the reactor was 430° C. during calcination. Upon completion of calcination, a liquid mixture of toluene and methanol having a toluene:methanol mole ratio thereof of 1:7.5 was combined with a nitrogen carrier gas in an amount sufficient to achieve a toluene:$N_2$ mole ratio in the feed of 0.11:1 (i.e. $N_2$ was fed at a rate of 70 cc/min.). The resulting toluene/methanol/$N_2$ feed was passed through the top of the reactor, maintained at 418° C. at a rate sufficient to achieve a contact time with each catalyst sample of 4.7 seconds at STP. The effluent stream was passed through a condenser and sample collectors and the liquid effluent collected for 60 minutes and anyalyzed by gas chromatography. The results of the analysis are summarized at Table 2, Run 1.

Part D

A sample of the untreated zeolite employed in Step A above was also subjected to elemental analysis to serve as a basis for comparison. The results of the analysis are summarized at Table 1.

COMPARATIVE EXAMPLE 1

A cesium exchanged sodium formed X-zeolite was prepared as follows:

An aqueous cesium hydroxide solution was prepared by dissolving 46.69 g of $CsOH \cdot XH_2O$ (83%) (0.26 moles CsOH) in 400 ml of deionized water at room temperature (20° C.). The resulting solution was divided into 4 100 ml portions which were successively admixed (in the absence of stirring) with a 50 g sample of Davison 4–8 mesh beads of sodium formed 13X zeolite to form 4 slurries. Each slurry was allowed to soak at 90° C. for different periods, namely, 16, 2, and 2 hours respectively, and the liquid portion of each solution was removed from the zeolite before adding the next portion. The resulting zeolite was filtered and washed with 500 ml of water and dried in air at 110° for 64 hours. A portion of the dried material was removed for elemental analysis and found to contain: Na (3.98%); Cs (22.7%); Al (9.53%); Si (13.62%); on a wt. % basis.

The resulting Cs exchanged zeolite was tested in accordance with Part C of Example 1 and the results summarized at Table 2, Run 2.

COMPARATIVE EXAMPLE 2

About 10 g of a Cs exchanged X-zeolite prepared in accordance with Comparative Example 1 was further exchanged with $BPO_4$ as follows:

An aqueous solution containing 25 g $CsOH \cdot XH_2O$ (83%) and 4 g $BPO_4$ dissolved in 400 ml of deionized water was prepared. A portion of this solution (200 ml) was then admixed with the zeolite, treated in accordance with Comparative Example 1 to form a slurry which was heated at 80° C. for 6 hours. The liquid portion of the slurry was removed, and the remaining 200 ml portion of the exchange solution admixed to form another slurry with the zeolite, at 80° C. for 16 hours. The liquid contents of this slurry were removed and the Cs/B/P-X zeolite washed with 500 ml water and dried at 110° C. for 24 hours. Elemental analysis of this zeolite showed the following weight percentages Cs (24.2%); B (0.001%); P (0.03%); Na (3.73%); Al (10.04%) and Si (14.73%). The resulting Cs/B/P-X zeolite was then tested in accordance with Part C of Example 1 and the results summarized at Table 2, Run 3.

TABLE 1

|  | Fresh X— Zeolite (Part D) | K Exchanged (Part A) | K/Cs Exchanged (Part B) |
|---|---|---|---|
| Wt. % |  |  |  |
| Na | 11.18 | 1.15 | 1.15 |
| K | N/A | 15.66 | 8.04 |
| Cs | N/A | N/A | 16.95 |
| Al | 12.27 | 11.91 | 10.89 |
| Si | 19.80 | 17.98 | 16.79 |
| Moles |  |  |  |
| Na | .49 | .05 ⎫ | .05 ⎫ |
| K | N/A | .40 ⎬ sum = .45 | .21 ⎬ sum = .39 |
| Cs | N/A | N/A | .13 ⎭ |
| Al | .45 | .44 | .40 |
| Si | .71 | .64 | .60 |
| Mole Ratio |  |  |  |
| Na:Al | 1.08:1 | .11:1 ⎫ | .12:1 ⎫ |
| K:Al | N/A | .91:1 ⎬ sum = 1.02:1 | .52:1 ⎬ sum = .96:1 |
| Cs:Al | N/A | N/A | .32:1 ⎭ |
| % of Na ions replaced by K | N/A | 89 | 54 ⎫ sum = 87% |
| % of Na ions replaced by Cs | N/A | N/A | 33 ⎭ |
| % Na ions remaining | N/A | N/A | 13 |

N/A — not applicable

TABLE 2

| Example No. | Run No. | Zeolite Catalyst Type | Methanol Conversion (%) | Toluene Conversion (%) | EB Selectivity (%) | EB + S Selectivity (%) | Styrene Selectivity (%) | EB + S Yield (%) |
|---|---|---|---|---|---|---|---|---|
| 1 | 1 | CsKNa—X | 99 | 37 | 85 | 87 | 2 | 32.2 |
| Comp. Ex. | 2 | CsNa—X | 69 | 30 | 74 | 78 | 4 | 23.4 |
| Comp. Ex. 2 | 3 | CsBPNa—X | 76 | 33 | 82 | 90 | 8 | 29.7 |

EB = ethylbenzene
S = styrene

DISCUSSION OF RESULTS

From the data of Table 1, it can be seen that about 87% of the sodium ions in sodium based zeolites were replaced with potassium and cesium. The first potassium exchange resulted in a displacement of about 89% of the sodium. Upon subsequent cesium exchange the sodium content remained substantially unchanged and the cesium exchange appears to have taken place by displacement of potassium. The replacement of all but about 13% of the sodium content of the zeolite thus contradicts the assertions of Unland et al that the practical limit of sodium exchange is about 60% and the theoretical limit for X-zeolites is 81%.

The data from Table 2 illustrates the effect on performance of a low sodium, high K/Cs content zeolite. Comparing the results of Example 1, Run 1, with Comparative Example 1, it can be seen that the combined presence of cesium and potassium versus cesium alone improves toluene conversion from 30 to 37% and improves the ethylbenzene and styrene selectivity from 78 to 87%. While the Cs/B/P-X zeolite of Comparative Example 2 increases styrene selectivity, the ethylbenzene+styrene yield (i.e. 29.7%) is still slightly less than the Cs/K-X zeolite.

The technique and advantages of replacing sodium by potassium and cesium has applicability to any X-or Y-type zeolite wherein the basicity of the catalyst is sought to be maximized. Consequently, the increase in styrene selectivity achieved by the combination of Cs/B/P-X exchanged zeolite can be complimented by the K/Cs sequential exchange of the present invention to also enhance toluene conversion if desired. Furthermore, as described in commonly assigned U.S. patent application Ser. Nos. 487,586 and 487,585 filed on even date herewith, the disclosures of which are herein incorporated by reference, other improved alkali metal/transition metal/BP containing zeolite catalysts can be prepared using the sequential high sodium replacement exchange of the present invention.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for alkylating toluene or toluene derivative with at least one alkylating agent which comprises reacting said alkylating agent with at least one compound represented by the structural formula:

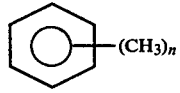
(I)

wherein n is a number which can vary from 1 to 6, said reaction being conducted in the presence of a catalyst composition comprising a crystalline aluminosilicate zeolite of the faujasite structure, under conditions sufficient to form a product comprising at least one compound represented by the structural formulae:

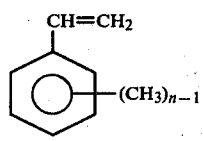
(II)

and

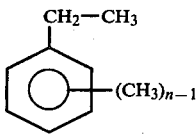
(III)

wherein n is a number which corresponds in value to that employed for n in structural formula I, and wherein in said crystalline aluminosilicate zeolite the $SiO_2:Al_2O_3$ mole ratio is from about 2 to about 8, and the electrovalence of the tetrahedra containing aluminum present therein is balanced by the inclusion in the crystal zeolite structure of cations comprising potassium and cesium which cations are present in amounts sufficient to achieve a potassium to aluminum mole ratio of from about 0.40:1 to about 0.60:1, and a cesium to aluminum mole ratio of from about 0.45:1 to about 0.30:1.

2. The process of claim 1 wherein said crystalline aluminosilicate is selected from the group consisting of zeolite-X of the sodium form or zeolite-Y of the sodium form, having at least 85% of the sodium initially present therein exchanged sequentially first for potassium and then for cesium.

3. The process of claim 2 wherein the zeolite is of the X-type.

4. The process of claim 1 wherein the presence of boron and phosphorus in the crystalline aluminosilicate is excluded.

5. The process of claim 2 wherein the mole ratio of potassium to aluminum in the zeolite is from about 0.50:1 to about 0.60:1, and the mole ratio of cesium to aluminum is from about 0.40:1 to about 0.30:1.

6. The process of claim 2 wherein at least 90% of the sodium initially present in the zeolite is exchanged for potassium and cesium.

7. The process of claim 1 wherein methanol is reacted with toluene to form a product comprising styrene.

8. The process of claim 1 wherein methanol is reacted with p-xylene to form p-methylstyrene.

9. The process of claim 7 wherein said reaction is conducted in the vapor phase by contacting a feed gas mixture comprising toluene and methanol, present in said gas mixture at a respective mole ratio of from about 1:0.05 to about 1:20, with said zeolite catalyst composition at a reaction temperature of from about 300° to about 550° C.

10. The process of claim 9 wherein said toluene:methanol mole ratio in said feed gas is from about 1:2 to about 1:10.

11. The process of claim 9 wherein said toluene:methanol mole ratio in said feed gas is from about 1:2 to about 1:5.

12. The process of claim 9 wherein said feed gas mixture contains an inert diluent gas.

13. The process of claim 12 wherein the inert diluent gas is nitrogen which is present in said feed gas mixture at a toluene:$N_2$ mole ratio of from about 0.4:1 to about 5:1.

* * * * *